US012691290B2

(12) United States Patent
Doerr

(10) Patent No.: US 12,691,290 B2
(45) Date of Patent: Jul. 28, 2026

(54) IMPLANTABLE MEDICAL DEVICE, IMPLANT COMMUNICATION SYSTEM AND COMMUNICATION METHOD

(71) Applicant: BIOTRONIK SE & Co. KG, Berlin (DE)

(72) Inventor: Thomas Doerr, Berlin (DE)

(73) Assignee: BIOTRONIK SE & Co. KG, Berlin (DE)

( * ) Notice: Subject to any disclaimer, the term of this patent is extended or adjusted under 35 U.S.C. 154(b) by 218 days.

(21) Appl. No.: 18/565,152

(22) PCT Filed: Jun. 2, 2022

(86) PCT No.: PCT/EP2022/065035
§ 371 (c)(1),
(2) Date: Nov. 29, 2023

(87) PCT Pub. No.: WO2023/274658
PCT Pub. Date: Jan. 5, 2023

(65) Prior Publication Data
US 2024/0269472 A1      Aug. 15, 2024

(30) Foreign Application Priority Data

Jun. 29, 2021    (EP) .................................... 21182313

(51) Int. Cl.
*A61N 1/37*          (2006.01)
*A61N 1/372*         (2006.01)
*A61N 1/375*         (2006.01)
(52) U.S. Cl.
CPC ..... *A61N 1/37229* (2013.01); *A61N 1/37235* (2013.01); *A61N 1/37252* (2013.01); *A61N 1/3754* (2013.01)

(58) Field of Classification Search
CPC ............ A61N 1/37217; A61N 1/37235; A61N 1/37264; A61N 1/37276
See application file for complete search history.

(56) References Cited

U.S. PATENT DOCUMENTS

| | | | |
|---|---|---|---|
| 2009/0228074 A1* | 9/2009 | Edgell ...................... | H01Q 1/40 607/60 |
| 2013/0154851 A1 | 6/2013 | Gaskill et al. | |
| 2015/0255858 A1* | 9/2015 | Li ............................ | A61N 5/04 343/702 |

OTHER PUBLICATIONS

EP Search Report mailed on Dec. 16, 2021, by the European Patent Office for Application No. EP21182313.3. (6 pages).

(Continued)

*Primary Examiner* — Amanda K Hulbert
(74) *Attorney, Agent, or Firm* — Buchanan Ingersoll & Rooney PC

(57)          ABSTRACT

The invention relates to an implantable medical device, in particular a diagnostic monitoring device, a pacemaker, a defibrillator and/or a neuro-stimulator, comprising a first wireless communication interface, operating in a first frequency band reserved for medical implants, a second wireless communication interface, operating in a second frequency band supported by consumer mobile communications devices, in particular smartphones and/or tablet computing devices, and a multi-band antenna connected to the first wireless communication interface and the second wireless communication interface, wherein the multi-band antenna is configured to operate in the first frequency band reserved for medical implants and in the second frequency band supported by consumer mobile communications devices. The invention further relates to an implant communication system, a method for updating an executable code of an implantable medical device and a computer program.

14 Claims, 2 Drawing Sheets

(56) References Cited

OTHER PUBLICATIONS

International Search Report (PCT/ISA/210) and Written Opinion (PCT/ISA/237) mailed on Aug. 26, 2022, by the European Patent Office as the International Searching Authority for International Application No. PCT/EP2022/065035. (12 pages).

* cited by examiner

IMPLANTABLE MEDICAL DEVICE, IMPLANT COMMUNICATION SYSTEM AND COMMUNICATION METHOD

CROSS-REFERENCE TO RELATED APPLICATIONS

This application is the United States National Phase under 35 U.S.C. § 371 of PCT International Patent Application No. PCT/EP2022/065035, filed on Jun. 2, 2022, which claims the benefit of European Patent Application No. 21182313.3, filed on Jun. 29, 2021, the disclosures of which are hereby incorporated by reference herein in their entireties.

TECHNICAL FIELD

The present invention relates to an implantable medical device, in particular a diagnostic monitoring device, a pacemaker, a defibrillator and/or a neuro-stimulator. The present invention further relates to an implant communication system.

BACKGROUND

Moreover, the present invention relates to a computer implemented method for communicating between an implantable medical device and an external communication device.

Active electronic implants are customarily equipped with Bluetooth Low Energy (BLE) radios to enable communication with commercially available smartphones and tablets.

Disadvantages of a Bluetooth Low Energy interface in implants are, on the one hand, an increased power consumption of this telemetry function especially if the connection is established frequently and, on the other hand, the changing standardizations and possible discontinuation of the Bluetooth Low Energy transmission protocol on the smartphone side over time.

On the other hand, the transmission modes and characteristics of MICS communication (transmission quality, power consumption, wireless wake-up, long-term stable life cycle) are considered to be advantageous over BLE communication for some use cases, so that MICS communication is to be preferred for some use cases while BLE connectivity is needed for alternative use cases.

The present disclosure is directed toward overcoming one or more of the above-mentioned problems, though not necessarily limited to embodiments that do.

SUMMARY

It is therefore an object of the present invention to provide an improved implantable medical device having dual communication capabilities supporting both BLE communication and MICS communication while maintaining compact housing dimensions.

At least the object is solved by an implantable medical device, in particular a diagnostic monitoring device, a pacemaker, a defibrillator and/or a neuro-stimulator having the features of claim 1.

At least the object is furthermore solved by an implant communication system having the features of claim 12.

In addition, at least the object is solved by a computer implemented method for communicating between an implantable medical device and an external communication device having the features of claim 13.

Moreover, at least the object is solved by a computer program of claim 14.

The present invention provides an implantable medical device, in particular a diagnostic monitoring device, a pacemaker, a defibrillator and/or a neuro-stimulator.

The implantable medical device comprises a first wireless communication interface, operating in a first frequency band reserved for medical implants and a second wireless communication interface, operating in a second frequency band supported by consumer mobile communications devices, in particular smartphones and/or tablet computing devices.

The implantable medical device further comprises a multi-band antenna connected to the first wireless communication interface and the second wireless communication interface, wherein the multi-band antenna is configured to operate in the first frequency band reserved for medical implants and in the second frequency band supported by consumer mobile communications devices.

The present invention further provides an implant communication system, comprising the implantable medical device according to the present invention and a programmer configured to communicate with the multi-band antenna of the implantable medical device in a first frequency band reserved for medical implants.

The implant communication system further comprises a consumer mobile communication device, in particular a smartphone or tablet computing device, configured to communicate with the multi-band antenna of the implantable medical device in a second frequency band supported by consumer mobile communications devices, in particular smartphones and/or tablet computing devices.

In addition, the present invention provides a computer implemented method for communicating between an implantable medical device and an external communication device.

The method comprises providing the implantable medical device with a first wireless communication interface, operating in a first frequency band reserved for medical implants.

Furthermore, the method comprises providing the implantable medical device with a second wireless communication interface, operating in a second frequency band supported by consumer mobile communications devices, in particular smartphones and/or tablet computing devices.

In addition, the method comprises providing the implantable medical device with a multi-band antenna connected to the first wireless communication interface and the second wireless communication interface, wherein the multi-band antenna communicates with a programmer in the first frequency band reserved for medical implants, and wherein the multi-band antenna communicates with the consumer mobile communications device in the second frequency band supported by consumer mobile communications devices.

It is an idea of the present invention to realize a simple and cost-effective antenna design for an implant that can communicate in both a first frequency band reserved for medical implants and a second frequency band supported by consumer mobile communications. Thereby the expense of housing a second antenna can be advantageously eliminated.

According to an aspect of the present invention, the first wireless communication interface and the second wireless communication interface are arranged in a metallic housing, in particular formed of titanium or stainless steel, of the implantable medical device. This way, the implantable medical device has dual band data transmission capability.

According to a further aspect of the present invention, the multi-band antenna is embedded in a non-metallic header, in particular formed of epoxy resin, of the implantable medical device. This ensures enhanced transmission characteristics due to lack of interference with the housing of the implantable medical device.

According to a further aspect of the present invention, the first wireless communication interface is connected to the multi-band antenna via a first antenna feed led via a first feedthrough from the metallic housing to the non-metallic header, and wherein the second wireless communication interface is connected to the multi-band antenna via a second antenna feed led via a second feedthrough from the metallic housing to the non-metallic header. Each antenna feed is thus connected to the multiband-antenna separately at a distinct connection point.

According to a further aspect of the present invention, the first wireless communication interface comprises a first radio and a first matching network configured to match a load impedance of the first radio to a combined input impedance of the first antenna feed and the multi-band antenna, and wherein the second wireless communication interface comprises a second radio and a second matching network configured to match a load impedance of the second radio to a combined input impedance of the second antenna feed and the multi-band antenna. The respective matching networks provide the advantage of being capable of adjusting the electrical length of the antenna without changing its mechanical length.

According to a further aspect of the present invention, the first wireless communication interface comprises a first radio, wherein the second wireless communication interface comprises a second radio, and wherein the first wireless communication interface and the second wireless communication interface are connected to a third matching network arranged in the metallic housing, said third matching network being configured to match a load impedance of the first radio and/or the second radio to a combined input impedance of the first antenna feed and the multi-band antenna and/or the second antenna feed and the multi-band antenna.

The third matching network thus advantageously is able to provide the functionality of being capable of adjusting the electrical length of the first and second antenna without changing their mechanical length.

According to a further aspect of the present invention, the third matching network is connected to the multi-band antenna via a single antenna feed led via a single feedthrough from the metallic housing to the non-metallic header. Both antennas thus share a single feed from the third matching network to the multi-band antenna such that only a single feedthrough from the metallic housing to the non-metallic header is needed.

According to a further aspect of the present invention, the third matching network is at least partially arranged in the non-metallic header of the implantable medical device. This allows the dimensions of the metallic housing of the implantable medical device to be reduced.

According to a further aspect of the present invention, the third matching network is part of the multi-band antenna. This advantageously reduces the number of electronic components within the housing.

According to a further aspect of the present invention, the non-metallic header is arranged on an outer surface of the metallic housing and is hermetically sealed against the metallic housing. This ensures enhanced transmission characteristics of the multi-band antenna due to lack of interference with the housing of the implantable medical device.

According to a further aspect of the present invention, the first wireless communication interface is configured to operate in a MICS-band, and wherein the second wireless communication interface is configured to operate in a Bluetooth, Bluetooth Low Energy and/or Bluetooth Mesh-band and/or use a Bluetooth, Bluetooth Low Energy and/or Bluetooth Mesh-band communication protocol. Thus, the implantable medical device has dual band data transmission capability.

The herein described features of the implantable medical device are also disclosed for the implant communication system, the computer implemented method for communicating between an implantable medical device and an external communication device and vice versa.

Additional features, aspects, objects, advantages, and possible applications of the present disclosure will become apparent from a study of the exemplary embodiments and examples described below, in combination with the Figures and the appended claims.

BRIEF DESCRIPTION OF THE DRAWINGS

For a more complete understanding of the present invention and advantages thereof, reference is now made to the following description taken in conjunction with the accompanying drawings. The present invention is explained in more detail below using exemplary embodiments, which are specified in the schematic figures of the drawings, in which.

DETAILED DESCRIPTION

Figure 1:
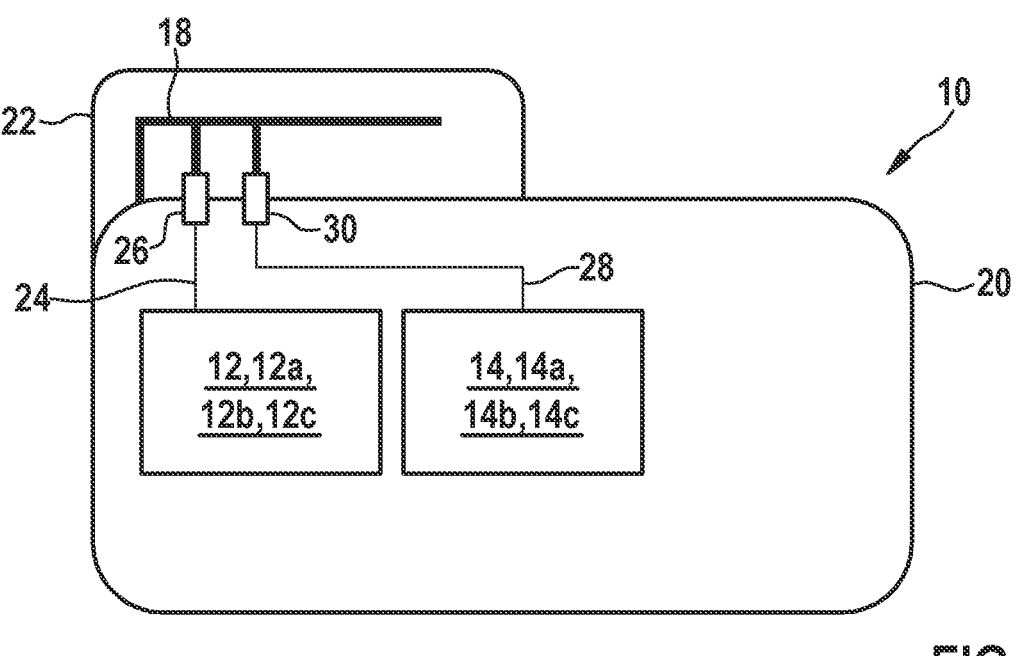
FIG. 1 shows a schematic view of an implantable medical device according to a first embodiment of the present invention.

The implantable medical device 10 of FIG. 1, in particular a diagnostic monitoring device, a pacemaker, a defibrillator and/or a neuro-stimulator comprises a first wireless communication interface 12, that operates in a first frequency band 12a reserved for medical implants.

Furthermore, the implantable medical device 10 comprises a second wireless communication interface 14, operating in a second frequency band 14a supported by consumer mobile communications devices 16, in particular smartphones and/or tablet computing devices.

The implantable medical device 10 moreover comprises a multi-band antenna 18 connected to the first wireless communication interface 12 and the second wireless communication interface 14, wherein the multi-band antenna 18 is configured to operate in the first frequency band 12a reserved for medical implants and in the second frequency band 14a supported by consumer mobile communications devices 16.

The first wireless communication interface 12 is configured to operate in a MICS-band, and wherein the second wireless communication interface 14 is configured to operate in a Bluetooth, Bluetooth Low Energy and/or Bluetooth Mesh-band.

The first wireless communication interface 12 and the second wireless communication interface 14 are arranged in a metallic housing 20, in particular formed of titanium, of the implantable medical device 10. Alternatively, the metallic housing 20 can be formed of stainless steel.

The multi-band antenna 18 is embedded in a non-metallic header 22, in particular formed of epoxy resin, of the implantable medical device 10. The first wireless communication interface 12 is connected to the multi-band antenna 18 via a first antenna feed 24 led via a first feedthrough 26 from the metallic housing 20 to the non-metallic header 22.

Furthermore, the second wireless communication interface 14 is connected to the multi-band antenna 18 via a second antenna feed 28 led via a second feedthrough 30 from the metallic housing 20 to the non-metallic header 22.

The first wireless communication interface 12 comprises a first radio 12b and a first matching network 12c configured to match a load impedance of the first radio 12b to a combined input impedance of the first antenna feed 24 and the multi-band antenna 18. Moreover, the second wireless communication interface 14 comprises a second radio 14b and a second matching network 14c configured to match a load impedance of the second radio 14b to a combined input impedance of the second antenna feed 28 and the multi-band antenna 18.

Figure 2:
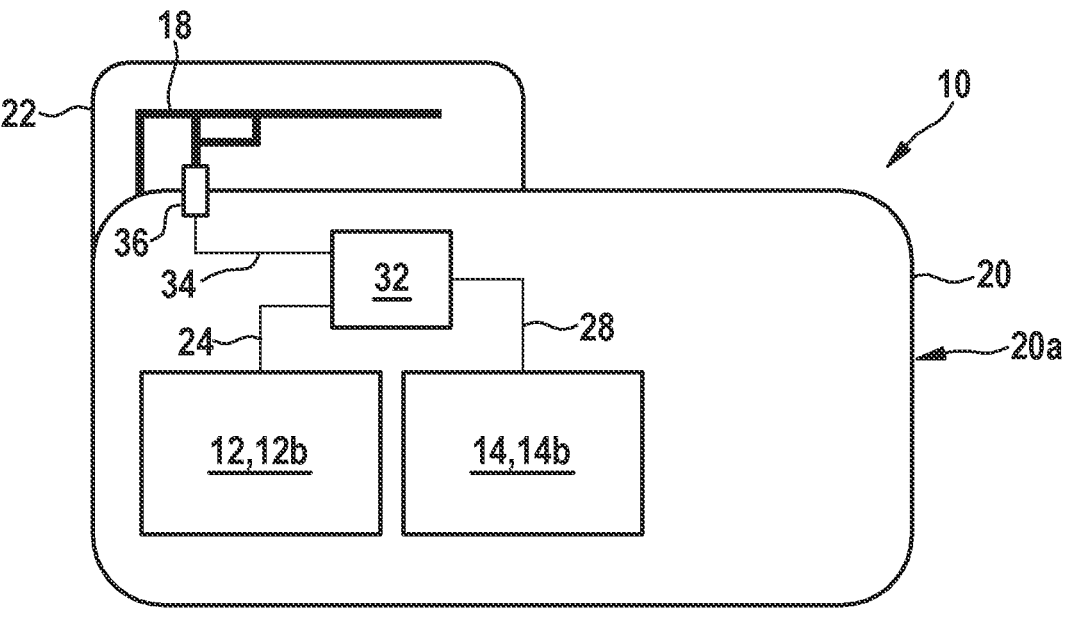
FIG. 2 shows a schematic view of an implantable medical device according to a second embodiment of the present invention.

FIG. 2 shows a schematic view of an implantable medical device according to a second embodiment of the present invention.

The first wireless communication interface 12 comprises a first radio 12b, wherein the second wireless communication interface 14 comprises a second radio 14b, and wherein the first wireless communication interface 12 and the second wireless communication interface 14 are connected to a third matching network 32 arranged in the metallic housing 20.

In addition, the third matching network 32 is configured to match a load impedance of the first radio 12b and/or the second radio 14b to a combined input impedance of the first antenna feed 24 and the multi-band antenna 18 and/or the second antenna feed 28 and the multi-band antenna 18. The third matching network 32 is further connected to the multi-band antenna 18 via a single antenna feed 34 led via a single feedthrough 36 from the metallic housing 20 to the non-metallic header 22.

According to the second embodiment of the present invention, the third matching network 32 is arranged in the metallic housing 20 of the implantable medical device 10. Alternatively, the third matching network 32 can be at least partially arranged in the non-metallic header 22 of the implantable medical device 10. Further alternatively, the third matching network 32 can be part of the multi-band antenna 18.

The non-metallic header 22 is arranged on an outer surface 20a of the metallic housing 20 and is hermetically sealed against the metallic housing 20.

Figure 3:
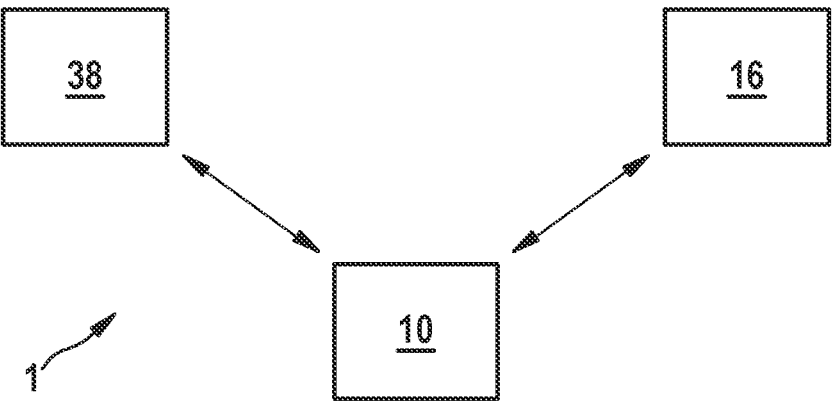
FIG. 3 shows a schematic view of an implant communication system according to embodiments of the present invention.

FIG. 3 shows a schematic view of an implant communication system 1 according to embodiments of the present invention. The implant communication system 1 comprises the implantable medical device 10 according to the present invention.

Furthermore, the implant communication system 1 comprises a programmer 38 configured to communicate with the multi-band antenna 18 of the implantable medical device 10 in a first frequency band 12a reserved for medical implants.

The implant communication system 1 moreover comprises a consumer mobile communication device 16, in particular a smartphone or tablet computing device, configured to communicate with the multi-band antenna 18 of the implantable medical device 10 in a second frequency band 14a supported by consumer mobile communications devices 16, in particular smartphones and/or tablet computing devices.

Figure 4:
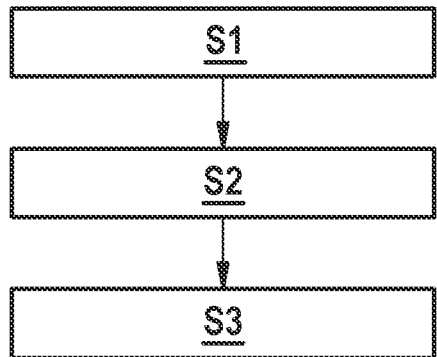
FIG. 4 shows a flowchart of a computer implemented method for communicating between an implantable medical device and an external communication device according to embodiments of the present invention.

FIG. 4 shows a flowchart of a computer implemented method for communicating between an implantable medical device and an external communication device according to embodiments of the present invention.

The method comprises comprising providing S1 the implantable medical device 10 with a first wireless communication interface 12, operating in a first frequency band 12a reserved for medical implants.

The method further comprises providing S2 the implantable medical device 10 with a second wireless communication interface 14, operating in a second frequency band 14a supported by consumer mobile communications devices 16, in particular smartphones and/or tablet computing devices.

In addition, the method comprises providing S3 the implantable medical device 10 with a multi-band antenna 18 connected to the first wireless communication interface 12 and the second wireless communication interface 14, wherein the multi-band antenna 18 communicates with a programmer 38 in the first frequency band 12a reserved for medical implants, and wherein the multi-band antenna 18 communicates with the consumer mobile communications device 16 in the second frequency band 14a supported by consumer mobile communications devices 16.

Further Embodiments:

A computer implemented method for communicating between an implantable medical device implanted into the human or animal body and an external communication device according to embodiments of the present invention.

The method comprises comprising providing S1 the implantable medical device 10 implanted into the human or animal body with a first wireless communication interface 12, operating in a first frequency band 12a reserved for medical implants.

The method further comprises providing S2 the implantable medical device 10 implanted into the human or animal body with a second wireless communication interface 14, operating in a second frequency band 14a supported by consumer mobile communications devices 16, in particular smartphones and/or tablet computing devices.

In addition, the method comprises providing S3 the implantable medical device 10 implanted into the human or animal body with a multi-band antenna 18 connected to the first wireless communication interface 12 and the second wireless communication interface 14, wherein the multi-band antenna 18 communicates with a programmer 38 in the first frequency band 12a reserved for medical implants, and wherein the multi-band antenna 18 communicates with the consumer mobile communications device 16 in the second frequency band 14a supported by consumer mobile communications devices 16.

It will be apparent to those skilled in the art that numerous modifications and variations of the described examples and embodiments are possible in light of the above teachings of the disclosure. The disclosed examples and embodiments are presented for purposes of illustration only. Other alternate embodiments may include some or all of the features disclosed herein. Therefore, it is the intent to cover all such modifications and alternate embodiments as may come within the true scope of this invention, which is to be given the full breadth thereof. Additionally, the disclosure of a range of values is a disclosure of every numerical value within that range, including the end points.

REFERENCE SIGNS 1 system
10 implantable medical device 12 first wireless communication interface
12a first frequency band
12b first radio
12c first matching network
14 second wireless communication interface
14a second frequency band
14b second radio
14c second matching network
16 consumer mobile communication device
18 multi-band antenna
20 metallic housing
20a outer surface of the metallic housing 20
22 non-metallic header
24 first antenna feed
26 first feedthrough
28 second antenna feed
30 second feedthrough
32 third matching network
34 single antenna feed
36 single feedthrough
38 programmer
S1-S3 method steps

The invention claimed is:

1. Implantable medical device, comprising:
a first wireless communication interface, operating in a first frequency band reserved for medical implants;
a second wireless communication interface, operating in a second frequency band supported by consumer mobile communications devices; and
a multi-band antenna connected to the first wireless communication interface and the second wireless communication interface, wherein the multi-band antenna is configured to operate in the first frequency band reserved for medical implants and in the second frequency band supported by consumer mobile communications devices.

2. Implantable medical device of claim 1, wherein the first wireless communication interface and the second wireless communication interface are arranged in a metallic housing of the implantable medical device.

3. Implantable medical device of claim 2, wherein the multi-band antenna is embedded in a non-metallic header of the implantable medical device.

4. Implantable medical device of claim 3, wherein the first wireless communication interface is connected to the multi-band antenna via a first antenna feed led via a first feedthrough from the metallic housing to the non-metallic header, and wherein the second wireless communication interface is connected to the multi-band antenna via a second antenna feed led via a second feedthrough from the metallic housing to the non-metallic header.

5. Implantable medical device of claim 4, wherein the first wireless communication interface comprises a first radio and a first matching network configured to match a load impedance of the first radio to a combined input impedance of the first antenna feed and the multi-band antenna, and wherein the second wireless communication interface comprises a second radio and a second matching network configured to match a load impedance of the second radio to a combined input impedance of the second antenna feed and the multi-band antenna.

6. Implantable medical device of claim 3, wherein the first wireless communication interface comprises a first radio, wherein the second wireless communication interface comprises a second radio, and wherein the first wireless communication interface and the second wireless communication interface are connected to a third matching network arranged in the metallic housing, said third matching network being configured to match a load impedance of the first radio and/or the second radio to a combined input impedance of the first antenna feed and the multi-band antenna and/or the second antenna feed and the multi-band antenna.

7. Implantable medical device of claim 6, wherein the third matching network is connected to the multi-band antenna via a single antenna feed led via a single feedthrough from the metallic housing to the non-metallic header.

8. Implantable medical device of claim 6, wherein the third matching network is at least partially arranged in the non-metallic header of the implantable medical device.

9. Implantable medical device of claim 6, wherein the third matching network is part of the multi-band antenna.

10. Implantable medical device of claim 3, wherein the non-metallic header is arranged on an outer surface of the metallic housing and is hermetically sealed against the metallic housing.

11. Implantable medical device of claim 1, wherein the first wireless communication interface is configured to operate in a MICS-band, and wherein the second wireless communication interface is configured to operate in a Bluetooth, Bluetooth Low Energy and/or Bluetooth Mesh-band.

12. Implant communication system, comprising:
the implantable medical device of claim 1;
a programmer configured to communicate with the multi-band antenna of the implantable medical device in a first frequency band reserved for medical implants; and
a consumer mobile communication device configured to communicate with the multi-band antenna of the implantable medical device in a second frequency band supported by consumer mobile communications devices.

13. Computer implemented method for communicating, comprising the steps of:
communicating between an implantable medical device and an external communication device while both the implantable medical device and the external communication are operating within a communication network environment including a first wireless communication interface, operating in a first frequency band reserved for medical implants, a second wireless communication interface, operating in a second frequency band supported by consumer mobile communications devices, wherein the implantable medical device includes a multi-band antenna connected to the first wireless communication interface and the second wireless communication interface, wherein the multi-band antenna communicates with a programmer in the first frequency band reserved for medical implants, and wherein the multi-band antenna communicates with the consumer mobile communications device in the second frequency band supported by consumer mobile communications devices.

14. Computer program with program code to perform the method of claim 13 when the computer program is executed on a computer.

* * * * *